June 1, 1937. L. PICKETT Re. 20,389
JAW BRACE
Original Filed Nov. 30, 1934
Fig. 1
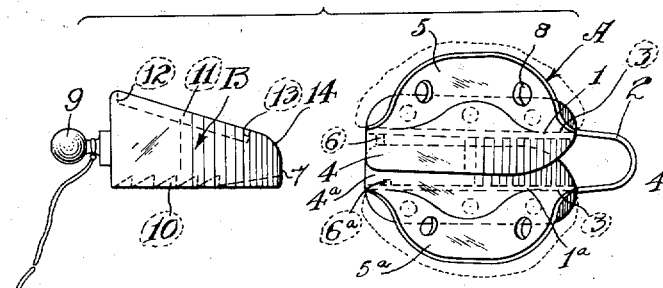
Fig. 2
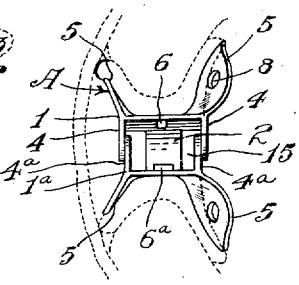
Fig. 3
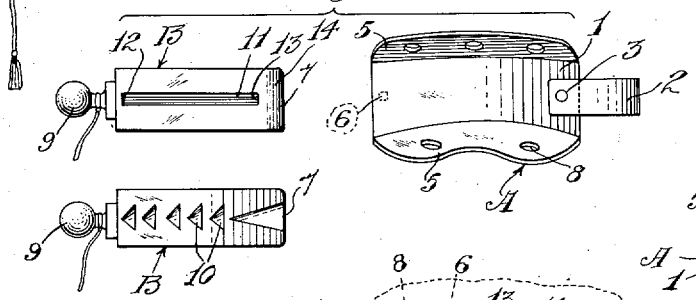
Fig. 4
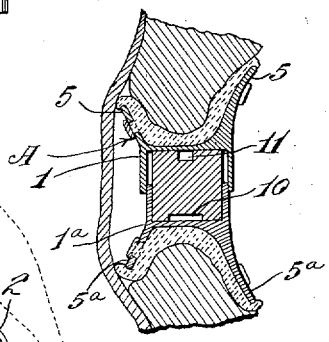
Fig. 6
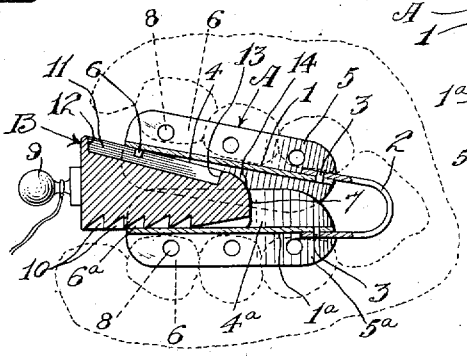
Fig. 5
Fig. 7
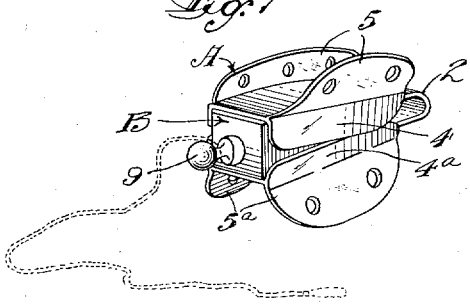
INVENTOR
Louis Pickett,
BY
Harry B. Rook,
ATTORNEY Reissued June 1, 1937

Re. 20,389

UNITED STATES PATENT OFFICE 20,389

JAW BRACE

Louis Pickett, Irvington, N. J.

Original No. 2,023,288, dated December 3, 1935, Serial No. 755,274, November 30, 1934. Application for reissue May 19, 1936, Serial No. 80,586

9 Claims. (Cl. 128—12)

My invention relates to devices for holding the mouth of a person open and is particularly adaptable for use by dentists while filling teeth, and while administering gas and by surgeons while removing tonsils or performing any other operation in the oral cavity.

In the drawing, Figure 1 is a composite side elevation of the parts of my device separated and in an inoperative position.

Figure 2 is a top plan view thereof,

Figure 3 is a front elevation of the body portion of my device showing its application in the mouth and also showing the plastic material as used therewith, Figure 4 is a bottom plan view of the wedge shaped member of Figure 2, Figure 5 is a vertical sectional view of my device in use, Figure 6 is a sectional view taken on the line 6—6 of Figure 5, and Figure 7 is a perspective view of my complete device.

My jaw brace consists of a female or body member A and a male member or spacer B, the two members A and B co-acting together so as to form a complete device. Member A consists of two jaw engaging members 1 and 1a of substantially channel formation which are held in spaced relation from each other by means of a U-shaped leaf spring 2, which is attached at its ends as at 3 to the respective jaw engaging members 1 and 1a. Spring 2 tends to maintain 1 and 1a in a predetermined relation with their opposed faces converging toward the spring and to yieldingly resist any tendency of them to become separated. The convergence of the jaw engaging members corresponds approximately to the convergence of the jaws of the open mouth, so that the device may be easily inserted into the mouth and will cause a minimum of obstruction to access to the mouth by the operator. Members 1 and 1a are provided with flanges 4 and 4a, respectively, flanges 4a being positioned in frictional contact with and within flanges 4. Both flanges 4 and 4a are of such vertical width and longitudinal length as to maintain contact with each other at all times and prevent relative lateral movement of the jaw engaging members and the spacer B.

Members 1 and 1a are also provided at the opposite sides from flanges 4 and 4a with secondary or auxiliary flanges 5 and 5a which are suitably molded in such a manner as to conform to the natural contour of the gums or jaws of a patient. These auxiliary flanges are also provided with apertures 8 the purposes of which are described below. Member 1 is provided with an inwardly disposed lug 6 and member 1a with a similarly inwardly turned lug 6a, the purposes of which are described below.

Member B is in the form of a wedge, the smaller end 7 adapted to be inserted within the box-like compartment 15 formed by the members 1 and 1a. Member B is also provided with a finger-piece 9 to which a cord may be attached for safety. A similar precaution may be taken with member A. One of the converging faces of B is provided with beveled notches 10, the inclined faces of which are in the direction of the small end 7 of member B which is also provided with longitudinal groove 11 on the other of its converging faces, the groove stopping short of the overall length of said face as shown at 12 and 13. The entering end of B is provided with a rounded surface 14.

Referring now to the operation of the device and the co-acting of the parts, in use a suitable plastic, such as wax, is placed within the confines of the flanges 5 and 5a of member A and the member is then inserted, spring end first, in the mouth cavity between the jaws, which come in contact therewith. The wax will be forced into conformation with the contour of the wearer's jaw or teeth and thus allow individual adaptation of the jaw brace in all cases, especially in instances of edentulous, partial or full dentition. By reason of entering the apertures in the flanges the wax or cushion will become attached to the flanges 5 and 5a and form a firm and suitable seat for the teeth or gums in connection with member A.

Member B is then inserted and forced into space 15 between members 1 and 1a in such a manner as to spread members 1 and 1a apart. The degree of spread is determined by the distance that member B is inserted and by the degree of angularity of the wedge. Lug 6 will engage slot 11 and lug 6a will engage the beveled notches 10, the foremost of which is in communication with an elongated V-shaped notch which acts as an entering notch and guide. It will be seen from this construction that after spacer B is inserted as described above it will be impossible for the spacer to be dislodged unintentionally and the spacer will thus hold members 1 and 1a in any fixed predetermined separated position. When it is desired to release member B from its compartment, a slight tilting action on the finger-piece will release lug 6a from the notches 10, and the wedge can easily be withdrawn and members 1 and 1a allowed to resume their original positions.

It is to be understood that in the drawing I have shown only one of a set of jaw-braces which include a right, set forth in the drawing, and a left jaw-brace.

Having thus described my invention, what I claim is:

1. A jaw-brace consisting of a pair of channel members adapted to support plastic material to prevent displacement of the jaw-brace in a patient's mouth and a means for spacing said channel members consisting of a U-shape flat resilient member; a means for spacing at will said members consisting of a wedge-like member, and a means for retaining said spacing which consists of a series of teeth on said wedge-shape member and a detent tooth attached to one of said jaw-supporting members and a channel-like slot in said wedge-shape member and a detent-like tooth for engagement with said slot.

2. A jaw brace comprising a pair of jaw engaging members connected at one end in converging relation toward said end corresponding to the convergence of the jaws of an open mouth and for movement toward and from each other, a wedge separably insertable between and from the other end of said jaw engaging members for varying the spacing of said jaw engaging members, and means for holding said wedge in adjusted position between said jaw engaging members.

3. A jaw brace comprising a pair of jaw engaging members hingedly connected together at one end and having their opposed inner surfaces converging toward said end, a wedge spacer insertable between and from the other end of said jaw engaging members and having opposed converging surfaces contacting with both of said converging surfaces of said members to adjust the distance between said jaw engaging members, and means for holding said spacer wedge in adjusted position.

4. A jaw brace comprising a pair of jaw engaging members, a spring hinge connecting said members together at one end with the opposed inner surfaces converging toward said end, said hinge consisting of a U-shaped leaf spring connected at each end to one of said members, and a spacer separably insertable between said members and having opposed converging surfaces and slidably contacting with both said opposed converging surfaces of said members to adjust the distance between said members.

5. A jaw brace comprising a pair of jaw engaging members, a spring hinge connecting said members together at one end with their opposed inner surfaces converging toward said end, said hinge normally yieldingly resisting movement of said members apart, and a wedge insertable between said members and having opposed converging surfaces slidably engaging both said opposed surfaces of said members to move them apart and adjust the distance between the members, said wedge and at least one of said members having cooperating portions to hold said wedge in adjusted position.

6. A jaw brace comprising a pair of jaw engaging members, a spring hinge connecting said members together at one end with their opposed inner surfaces converging toward said end, said hinge normally yieldingly resisting movement of said members apart, and a wedge insertable between said members and having opposed converging surfaces slidably engaging both said opposed surfaces of said members to move them apart and adjust the distance between the members, said wedge and at least one of said members having cooperating projections and recesses to hold said wedge in adjusted position.

7. A jaw brace comprising a pair of jaw engaging members, a U-shaped leaf spring connected at each end to one of said members for connecting said members in converging relation and for movement toward and from each other, said members having flanges at opposite sides of the opposed inner surfaces of said members, and a spacer comprising a block between and slidably contacting with both said surfaces and said flanges to adjust the distance between said members, said flanges preventing relative lateral movement of said members and said spacer.

8. A jaw brace comprising a pair of jaw engaging members hingedly connected together adjacent one end with continuous opposed inner surfaces extending toward said end, a spacer between said members and having a continuous elongate surface in slidable engagement with each of said surfaces of said members from the free ends toward the connected ends to adjust the distance between said members, said spacer and at least one of said members having releasably cooperating portions to hold said spacer in adjusted position between said members.

9. A jaw brace comprising a pair of jaw engaging members hingedly connected together adjacent one end with the continuous opposed inner surfaces extending toward said end, a spacer between said members and having a continuous elongate surface in slidable engagement with each of said surfaces of said members from the free ends toward the connected ends to adjust the distance between said members, and means for holding said spacer in adjusted position.

LOUIS PICKETT.